US010358651B2

(12) United States Patent
Loque et al.

(10) Patent No.: US 10,358,651 B2
(45) Date of Patent: Jul. 23, 2019

(54) MODIFIED PLANTS AND METHODS FOR PRODUCING MODIFIED LIGNIN BY MODULATING EXPRESSION OF ACYLTRANSFERASES

(71) Applicant: The Regents of the University of California, Oakland, CA (US)

(72) Inventors: Dominique Loque, Albany, CA (US); Aymerick Guillaume Eudes, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/056,982

(22) Filed: Feb. 29, 2016

(65) Prior Publication Data
US 2016/0251672 A1 Sep. 1, 2016

Related U.S. Application Data

(60) Provisional application No. 62/126,408, filed on Feb. 27, 2015.

(51) Int. Cl.
*C12N 15/82* (2006.01)
*C08H 7/00* (2011.01)
*C12N 9/10* (2006.01)
*C07G 1/00* (2011.01)

(52) U.S. Cl.
CPC ........... *C12N 15/8255* (2013.01); *C07G 1/00* (2013.01); *C08H 6/00* (2013.01); *C12N 9/1025* (2013.01); *C12Y 203/00* (2013.01)

(58) Field of Classification Search
None
See application file for complete search history.

(56) References Cited

U.S. PATENT DOCUMENTS

| 2003/0070188 A1 | 4/2003 | Havkin-Frenkel | |
|---|---|---|---|
| 2011/0003978 A1 | 1/2011 | Ralph | |
| 2012/0117694 A1 | 5/2012 | Liu | |
| 2013/0078683 A1* | 3/2013 | Loque | C12P 13/02 435/129 |
| 2013/0203973 A1* | 8/2013 | Wilkerson | C08H 6/00 530/505 |
| 2013/0219547 A1 | 8/2013 | Wilkerson | |
| 2014/0011984 A1 | 1/2014 | Ralph | |
| 2015/0020234 A1 | 1/2015 | Wilkerson | |

FOREIGN PATENT DOCUMENTS

WO    WO2003071861 A3    9/2003

OTHER PUBLICATIONS

D'Auria, 2006, Curr. Op. Plant Biology, 9:331-340.*
Sander et al, 2011, Planta, 233:1157-1171.*
Eudes et al, 2014, Curr. Op. Biotech., 26:189-198.*
Bartley et al, 2013, Plant Physiology, 161:1615-1633.*
Vanholme et al, 2010, Plant Physiol., 153: 895-905.*
Eudes et al, 2012 Plant Biotechnology Journal, 10:609-620.*
Yang et al, 2004, MPMI, 17:81-89.*
Eudes, A, George A, Mukerjee P, Kim JS, Pollet B, Benke PI, Yang F, Mitra P, Sun L, Cetinkol OP et al.: Biosynthesis and incorporation of side-chain-truncated lignin monomers to reduce lignin polymerization and enhance saccharification. Plant Biotechnol J (2012), 10:609-620.
Zhang, K, Bhuiya M-W, Pazo JR, Miao Y, Kim H, Ralph J, Liu C-J: An engineered monolignol 4-O-methyltransferase depresses lignin biosynthesis and confers novel metabolic capability in *Arabidopsis*. Plant Cell Online (2012), 24:3135-3152.
Vanholme, R, Storme V, Vanholme B, Sundin L, Christensen JH, Goeminne G, Halpin C, Rohde A, Morreel K, Boerjan W: A systems biology view of responses to lignin biosynthesis perturbations in *Arabidopsis*. Plant Cell (2012), 24:3506-3529.
Zhong, R, Lee C, Ye Z-H: Evolutionary conservation of the transcriptional network regulating secondary cell wall biosynthesis. Trends Plant Sci (2010), 15:625-632.
Berthet, S, Demont-Caulet N, Pollet B, Bidzinski P, Cezard L, Le Bris P, Borrega N, Herve J, Blondet E, Balzergue S et al.: Disruption of LACCASE4 and 17 results in tissue-specific alterations to lignification of *Arabidopsis thaliana* stems. Plant Cell (2011), 23:1124-1137.
Bollhoener, B, Prestele J, Tuominen H: Xylem cell death: emerging understanding of regulation and function. J Exp Botany (2012), 63:1081-1094.
Ko, J-H, Kim H-T, Hwang I, Han K-H: Tissue-type-specific transcriptome analysis identifies developing xylem-specific promoters in poplar Plant Biotechnol J (2012), 10:587-596.
Kubo, M, Udagawa M, Nishikubo N, Horiguchi G, Yamaguchi M, Ito J, Mimura T, Fukuda H, Demura T: Transcription switches for protoxylem and metaxylem vessel formation. Genes Develop (2005), 19:1855-1860.
Mitsuda, N, Iwase A, Yamamoto H, Yoshida M, Seki M, Shinozaki K, Ohme-Takagi M: NAC transcription factors, NST1 and NST3, are key regulators of the formation of secondary walls in woody tissues of *Arabidopsis*. Plant Cell Online (2007), 19:270-280.
Yang, F, Mitra P, Zhang L, Prak L, Verhertbruggen Y, Kim JS, Sun L, Zheng K, Tang K, Auer M et al.: Engineering secondary cell wall deposition in plants. Plant Biotechnol J (2013), 11:325-335.
Bianchetti, CM, Harmann CH, Takasuka TE, Hura GL, Dyer K, Fox BG: Fusion of dioxygenase and lignin-binding domains in a novel secreted enzyme from cellulolytic *Streptomyces* sp. SirexAA-E. J Biol Chem (2013), 288:18574-18587.
Elumalai, S, Tobimatsu Y, Grabber JH, Pan X, Ralph J: Epigallocatechin gallate incorporation into lignin enhances the alkaline delignification and enzymatic saccharification of cell walls. Biotechnol Biofuels (2012), 5:59.
Grabber, J, Schatz P, Kim H, Lu F, Ralph J: Identifying new lignin bioengineering targets: 1.Monolignol-substitute impacts on lignin formation and cell wall fermentability. BMC Plant Biol (2010), 10:114.
Grabber, JH, Hatfield RD, Lu F, Ralph J: Coniferyl ferulate incorporation into lignin enhances the alkaline delignification and enzymatic degradation of cell walls. Biomacromolecules (2008), 9:2510-2516.

(Continued)

*Primary Examiner* — Jason Deveau Rosen
(74) *Attorney, Agent, or Firm* — Robin C. Chiang; Lawrence Berkeley National Laboratory

(57) ABSTRACT

The present invention provides for novel compositions and methods of producing modified lignin by modulating expression of acyltransferases.

12 Claims, 6 Drawing Sheets

(56) References Cited

OTHER PUBLICATIONS

Grabber, JH, Ress D, Ralph J: Identifying new lignin bioengineering targets: impact of epicatechin, quercetin glycoside, and gallate derivatives on the lignification and fermentation of maize cell walls. J Agric Food Chem (2012), 30:5152-5160.

Tobimatsu, Y, Elumalai S, Grabber JH, Davidson CL, Pan X, Ralph J: Hydroxycinnamate conjugates as potential monolignol replacements: in vitro lignification and cell wall studies with rosmarinic acid. ChemSusChem (2012), 5:676-686.

Vanholme R, Morreel K, Darrah C, Oyarce P, Grabber JH, Ralph J, Boerjan W: Metabolic engineering of novel lignin in biomass crops. New Phytol (2012), 196:978-1000.

Grabber, JH, Hatfield RD: Methyl esterification divergently affects the degradability of pectic uronosyls in nonlignified and lignified maize cell walls. J Agric Food Chem (2005), 53:1546-1549.

Grabber, JH, Hatfield RD, Ralph J: Apoplastic pH and monolignol addition rate effects on lignin formation and cell wall degradability in maize. J Agric Food Chem (2003), 51:4984-4989.

Chen, F, Tobimatsu Y, Jackson L, Nakashima J, Ralph J, Dixon RA: Novel seed coat lignins in the Cactaceae: structure, distribution and implications for the evolution of lignin diversity. Plant J (2012), 73:201-211.

Fu, C, Mielenz JR, Xiao X, Ge Y, Hamilton CY, Rodriguez M Jr, Chen F, Foston M, Ragauskas A, Bouton J et al.: Genetic manipulation of lignin reduces recalcitrance and improves ethanol production from switchgrass. Proc Natl Acad Sci USA (2011), 108:3803-3808.

Van Doorsselaere, J, Baucher M, Chognot E, Chabbert B, Tollier M-T, Petit-Conil M, Leple' J-C, Pilate G, Cornu D, Monties B et al.: A novel lignin in poplar trees with a reduced caffeic acid/5-hydroxyferulic acid O-methyltransferase activity. Plant J (1995), 8:855-864.

Sederoff, RR, MacKay JJ, Ralph J, Hatfield RD: Unexpected variation in lignin. Curr Opin Plant Biol (1999), 2:145-152.

Stewart, C Jr, Vickery CR, Burkart MD, Noel JP: Confluence of structural and chemical biology: plant polyketide synthases as biocatalysts for a bio-based future. Curr Opin Plant Biol (2013), 16:365-372.

Satake, H, Ono E, Murata J: Recent advances in the metabolic engineering of lignin biosynthesis pathways for the production of transgenic plant-based foods and supplements. J Agric Food Chem (2013), 61:11721-11729.

Colquhoun, TA, Clark DG: Unraveling the regulation of floral fragrance biosynthesis. Plant Signal Behav (2011), 6:378-381.

Withers, S, Lu F, Kim H, Zhu Y, Ralph J, Wilkerson CG: Identification of grass-specific enzyme that acylates monolignols with p-coumarate. J Biol Chem (2012), 287:8347-8355.

Yang, Q, Trinh HX, Imai S, Ishihara A, Zhang L, Nakayashiki H, Tosa Y, Mayama S: Analysis of the involvement of hydroxyanthranilate hydroxycinnamoyltransferase and caffecyl-CoA 3-O-methyltransferase in phytoalexin biosynthesis in oat. Mol Plant Microbe Interact (2004), 17:81-89.

Hensel, A, Deters AM, Muller G, Stark T, Wittschier N, Hofmann T: Occurrence of Nphenylpropenoyl-L-amino acid amides in different herbal drugs and their influence on human keratinocytes, on human liver cells and on adhesion of Helicobacter pylori to the human stomach. Planta Med (2007), 73:142-150 (Abstract).

Schmidt, A, Grimm R, Schmidt J, Scheel D, Stack D, Rosahl S: Cloning and expression of a potato cDNA encoding hydroxycinnamoyl-CoA:tyramine N-(hydroxycinnamoyl)transferase. J Biol Chem (1999), 274:4273-4280.

Vetting, MW, SdC LP, Yu M, Hegde SS, Magnet S, Roderick SL, Blanchard JS: Structure and functions of the GNAT superfamily of acetyltransferases. Arch Biochem Biophys (2005), 433:212-226.

Ralph, J, Akiyama T, Coleman H, Mansfield S: Effects on lignin structure of coumarate 3-hydroxylase downregulation in poplar. Bioenergy Research (2012), 5:1009-1019.

Podstolski, A, Havkin-Frenkel D, Malinowski J, Blount JW, Kourteva G, Dixon RA: Unusual 4-ydroxybenzaldehyde synthase activity from tissue cultures of the vanilla orchid Vanilla planifolia. Phytochemistry (2002), 61:611-620.

Pak, FE, Gropper S. Dai WD, Havkin-Frenkel D, Belanger FC: Characterization of a multifunctional methyltransferase from the orchid Vanilla planifolia. Plant Cell Rep (2004), 22:959-966.

Siebert, M, Sommer S, Li SM, Wang ZX, Severin K, Heide L: Genetic engineering of plant secondary metabolism. Accumulation of 4-hydroxybenzoate glucosides as a result of the expression of the bacterial ubiC gene in tobacco. Plant Physiol (1996), 112:811-819.

Viitanen, PV, Devine AL, Khan MS, Deuel DL, Van Dyk DE, Daniell H: Metabolic engineering of the chloroplast genome using the *Escherichia coli* ubiC gene reveals that chorismate is a readily abundant plant precursor for p-hydroxybenzoic acid biosynthesis. Plant Physiol (2004), 136:4048-4060.

Alt, S, Burkard N, Kulik A, Grond S, Heide L: An artificial pathway to 3,4-dihydroxybenzoic acid allows generation of new aminocoumarin antibiotic recognized by catechol transporters of *E. coli*. Chem Biol (2011), 18:304-313.

Muir, RM, Ibanez AM, Uratsu SL, Ingham ES, Leslie CA, McGranahan GH, Batra N, Goyal S, Joseph J, Jemmis ED et al.: Mechanism of gallic acid biosynthesis in bacteria (*Escherichia coli*) and walnut (*Juglans regia*). Plant Mol Biol (2011), 75:555-565.

\* cited by examiner

MODIFIED PLANTS AND METHODS FOR PRODUCING MODIFIED LIGNIN BY MODULATING EXPRESSION OF ACYLTRANSFERASES

RELATED PATENT APPLICATIONS

The application claims priority to U.S. Provisional Patent Application Ser. No. 62/126,408, filed Feb. 27, 2015; which is incorporated herein by reference.

STATEMENT OF GOVERNMENTAL SUPPORT

This invention was made with government support under Contract No. DE-AC02-05CH11231 awarded by the United States Department of Energy. The government has certain rights in the invention.

FIELD OF THE INVENTION

This invention relates generally to modifying biomass by modulating expression of acyltransferases.

BACKGROUND OF THE INVENTION

In its effort to make cellulosic biofuel production more cost-effective, the bioenergy field has necessarily focused much of its attention on plant cell walls. Lignin, a major component of cell walls, is the third most-abundant biopolymer and the largest available resource of natural aromatic polymers (FIG. 1A). It is mainly composed of the monolignols p-coumaryl, coniferyl, and sinapyl alcohols which give rise to the p-hydroxyphenyl (H), guaiacyl (G) and syringyl (S) lignin units [1]. Unfortunately, it is also the primary contributor to the high cost of lignocellulosic sugar production, because cell wall polysaccharides are encrusted with lignin which make them highly resistant to extraction and enzymatic hydrolysis [1, 2]. Moreover, lignin has almost no commercial value aside from its role as a source of heat, and it is generally treated as a waste product [3].

Lignin has been a target of genetic manipulation for several decades because its content in biomass is inversely correlated with its forage digestibility and kappa value in the pulping industry [4, 5]. Lignin biosynthesis is well-characterized and all the enzymes required for the synthesis of its three major building blocks—called monolignols—are well-known and highly-conserved in all vascular plants [6, 7]. Unfortunately, lignin cannot be simply removed from growing plants without causing deleterious developmental effects [8]. Genetic manipulation trials using natural mutants or silencing strategies have failed because they drastically reduced lignin content in a non-selective way. Nevertheless, there are cases in which mild genetic manipulations have been used to moderately reduce lignin content or modify its composition in biomass, modestly improving saccharification efficiency, forage digestibility, and pulping yield [9]. These approaches are still rather limited.

Novel strategies need to be developed to reduce lignin content further, without altering plant development or causing undesirable effects. Classical lignin-modification methods typically repress the expression or activity of lignin biosynthetic genes. They require identification of natural defective alleles, the screening of single-nucleotide polymorphisms (SNPs) from mutant populations (usually a labor-intensive process) or the development of RNAi-based gene-silencing approaches. The limit of all these approaches is the lack of tissue specificity because every cell carries the same defective allele or silenced gene since RNAi move from cell-to-cell and affect most of the tissues in the plant [10]. Moreover, they affect not only the lignin biosynthesis pathway, but also have indirect effects on other metabolic routes connected to the phenylpropanoid and monolignol pathways. The phenylpropanoid pathway, for example, generates a wide array of secondary metabolites that contribute to all aspects of plant development and plant responses to biotic and abiotic stresses [11].

Recently, researchers have developed more elaborate approaches for lignin modification and employed tissue-specific promoters to reduce the risk of disturbing other phenylpropanoid-derived pathways in non-lignified tissues [12, 13]. The utilization of such promoters is challenging because most of the lignin genes (PAL, C4H, 4CL, HCT, C3H, among others) belong to the phenyl-propanoid pathway [14]. Use of the corresponding promoters for engineering purposes may affect the bio-synthesis of associated metabolites such as flavonoids, suberin, coumarins, phenolic volatiles, or hydrolyzable tannins. On the other hand, most promoters of secondary cell-wall biosynthetic genes (CesAs, GTs, or lignin genes) [15] are expressed in both vascular bundles and inter-fascicular xylem fibers, raising concerns that lignin modification would affect the integrity of vessels. Vessel-specific and fiber-specific genes (and corresponding promoters) were identified in few species and their number remains limited (VNDs, NSTs, SNDs, WNDs, Lac17 [16-20]). Single-promoter-driven transgene expression, which can confer both adequate spatio-temporal expression and transcription strength for optimal engineering, is consequently difficult to achieve. Furthermore, using several copies of the same promoters for engineering may lead to silencing issues, including the silencing of endogenous promoters if they share high sequence similarities. However, adjusting transgene expression to optimal levels and restricting it to specific cells at particular developmental stages will reduce undesirable side effects. Ideally, newly emerging techniques will be combined with tissue-specific promoters to meet the challenges associated with plant metabolic engineering, particularly those involving manipulation of the phenylpropanoid pathway. In this review, we will address important aspects in the engineering of lignin that involve the manipulation of its content, composition, and distribution. First we will focus on emerging synthetic biology tools that can fine-tune transgene expression and improve their spatio-temporal expression. We will conclude with the presentation of novel approaches for manipulation of lignin to make it more suitable for various applications such as bioenergy and biochemical production (FIG. 1B).

SUMMARY OF THE INVENTION

The present invention provides a genetically modified plant comprising an acyltransferase wherein the acyltransferase catalyzes the addition of an acceptor to a lignin carrier moiety; and optionally a lignin polymer comprising the acceptor. In some embodiments, the lignin polymers have an average molecular weight that is lower than the average molecular weight of the lignin polymers of the plant that is not genetically modified.

The present invention provides for a cell wall, or biomass obtained from the genetically modified plant comprising the lignin polymer comprising the acceptor.

The present invention also provides for a method to produce lignin modified with an acceptor, comprising: (a) providing a genetically modified plant of the present invention, (b) growing the genetically modified plant, (c) isolating the lignin of the plant from the rest of the plant, and (d) optionally separating the acceptors from the lignin.

In some embodiments, the genetically modified plant comprises a nucleic acid encoding a promoter operatively linked to an open reading frame (ORF) encoding the acyl-transferase.

Suitable acyltransferases are described herein and in the references cited herein. In some embodiments, the acyltransferase is a BAHD acyltransferase, GCN5-related N-acetyltransferase (GNAT), serine carboxypeptidase, or monolignol 4-O-methyltransferase. In some embodiments, the BAHD acyltransferase is hydroxycinnamoyl/benzoyl-CoA:anthranilate N-hydroxycinnamoyl/benzoyltransferase (HCBT), such as from carnation, or hydroxycinnamoyl-CoA:hydroxyanthranilate N-hydroxycinnamoyltransferase (HHT), such as from oats. Suitable acyltransferase are disclosed in U.S. Patent Application Pub. Nos. 20110003978, 20120117694, 20130203973, 20130219547, 20140011984, 20150020234, and 20150020234.

Suitable acceptors are described herein, for example, in FIGS. 3A-3G.

This invention allows for the enrichment of biomass with valuable compounds by expressing or overexpressing specific acyltransferases capable of coupling valuable molecules to hydroxycinnamoyl-CoAs in plants (e.g. BAHD acyltransferases, GCN5-related N-acetyltransferases (GNATs), and serine carboxypeptidase). The valuable compounds are linked "weakly" to the extremities of lignin chains (such as ester or amide bonds) and therefore can be cleaved easily during biomass processing. The invention would add value to the waste lignin streams generated by agroindustries that process biomass for bioenergy or pulp and paper manufacturing.

Very few technologies make use of lignin although it represents up to 25% of plant biomass and could be further enhanced. Lignin is separated from polysaccharides during biomass processing and usually burned to create energy. With this invention, lignin can be used to trap valuable molecules other than the conventional lignin building blocks during plant development and cell wall formation. This invention would add extra value to the lignin waste streams since the valuable molecules can be recovered.

This invention is possible with the recent identification of acyl-transferases that use intermediates of the lignin pathway as donors. These enzymes could be used to attached various acceptors (i.e. valuable molecules) onto the lignin pathway intermediates (carrier moieties) and hence build more valuable lignin polymers. One important point in the selection of valuable chemicals (acceptor moieties) is to select or modify them to be recalcitrant to lignin polymerization and only the other moieties (carrier moieties/lignin pathway intermediates) will be polymerized with other monolignols and growing lignin polymers.

We want to valorize lignin by decorating it with valuable molecules that will be easily shaved from the polymer for downstream applications. Potential valuable candidates could be benzoate, cinnamate, tyramine, methyl-anthranilate ester, and the like. These valuable compounds, such as aromatics, could be converted by other technologies (chemical and biological) into BTX (benzene, toluene and xylenes) that are mostly produced from petroleum products.

Based on the replacement strategy used and incorporation rate of these novel monolignols, the amount of valuable chemical could represent up to 50% of the lignin content.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
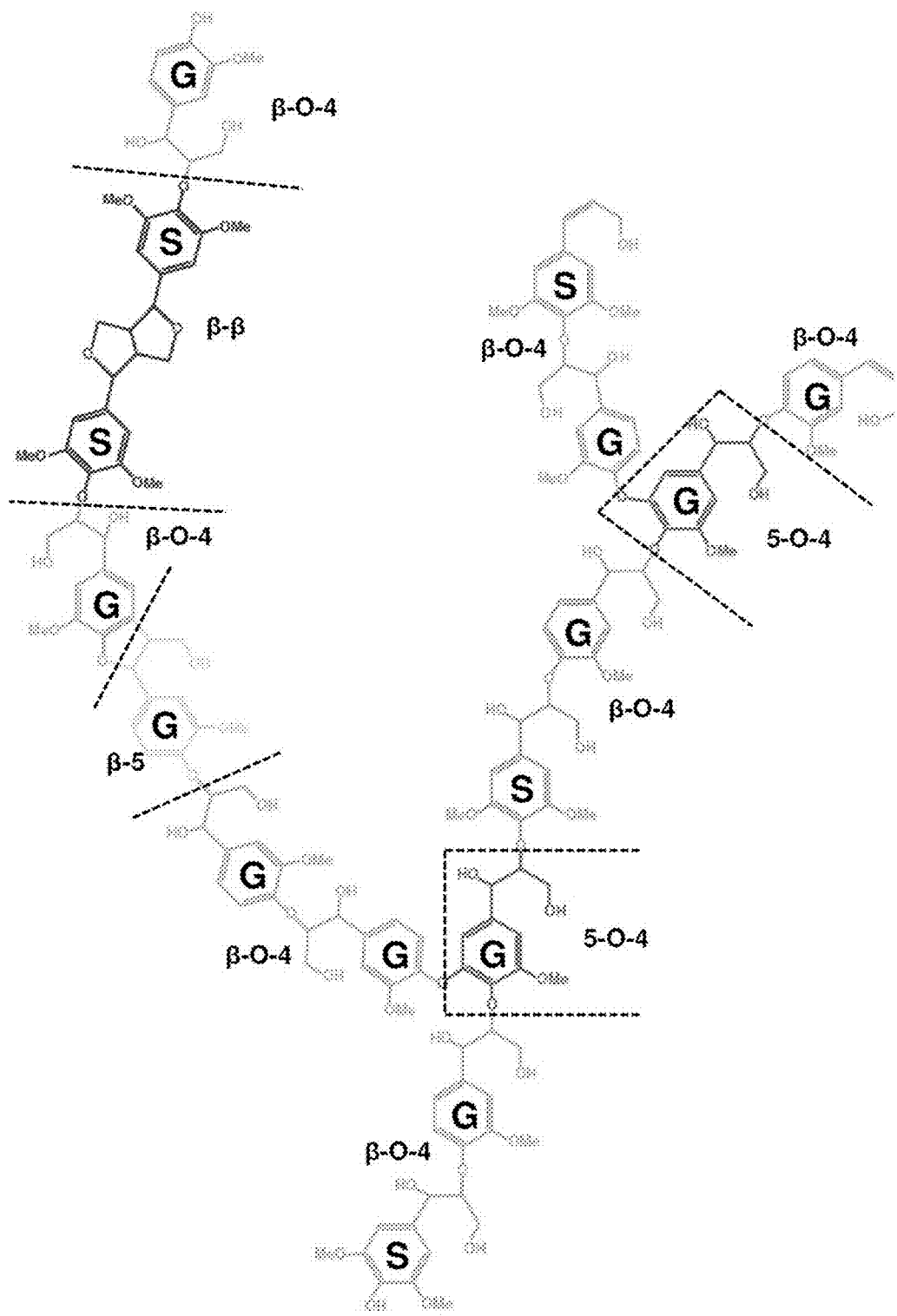
FIG. 1A. Lignin polymer models for wild type plants. β-O-4: β-ether; β-5: phenylcoumaran; β-β: resinol; 5-O-4: β-ether; S: syringyl; G: guaiacyl.

The foregoing aspects and others will be readily appreciated by the skilled artisan from the following description of illustrative embodiments when read in conjunction with the accompanying drawings.

Lignin is one of the most abundant aromatic biopolymers and a major component of plant cell walls. It occurs via oxidative coupling of monolignols, which are synthesized from the phenylpropanoid pathway. Lignin is the primary material responsible for biomass recalcitrance, has almost no industrial utility, and cannot be simply removed from growing plants without causing serious developmental defects. Fortunately, recent studies report that lignin composition and distribution can be manipulated to a certain extent by using tissue-specific promoters to reduce its recalcitrance, change its biophysical properties, and increase its commercial value. Moreover, the emergence of novel synthetic biology tools to achieve biological control using genome bioediting technologies and tight regulation of transgene expression opens new doors for engineering. This review focuses on lignin bioengineering strategies and describes emerging technologies that could be used to generate tomorrow's bioenergy and biochemical crops.

Synthetic Biology Tools for Lignin Engineering

Genome Bioediting Tools

Creation of biological tools for targeted genome manipulation is an important goal in molecular biology. Such tools have an essential role in reverse genetics, and their development will have fundamental implications in bio-technology applications ranging from gene therapy to the production of chimeric plants. For example, tissue-specific promoters could be used to express these novel biological tools to create SNPs in key genes to render them defective only in target tissues. Using such an approach, the target genes present in meristematic and meiotic cells would be SNP-free. Major progress has been made in the development of crucially important genome bioediting tools, as exemplified by zinc-finger nucleases (ZFNs), transcription activator-like effector nucleases (TALENs), and the clustered, regularly interspaced, short palindromic repeats (CRISPR)/CRISPR-associated (CAS) system [21]. These various genome bioediting tools share a common principle: the utilization of engineered endonucleases is associated with customizable DNA binding elements. Directed by the DNA binding elements, endonucleases cleave at the target loci and generate DNA double-strand breaks (DSBs). DSBs are subsequently repaired by one of the two cellular DNA repair mechanisms: non-homologous end joining (NHEJ), or homologous recombination (HR). Repair by NHEJ frequently introduces mutations, resulting in gene interruption at the target locus.

DNA-binding elements in ZFNs and TALENs are composed of modular protein motifs [22-24]. An individual ZF primarily recognizes DNA sites of 3 bp. To establish recognition specificity, arrays of ZF units connected by linker sequences recognize DNA sequences 9-18 bp in length [23]. The DNA-binding motifs in TALEs present as near-perfect repeats, typically 34 amino acids in length. Repeat-variable di-residues (RVDs), usually occurring at residues 12 and 13, designate the base pair or nucleotide recognition code in a one-to-one manner [22-24]. Since the first demonstration of yellow gene interruption in *Drosophila melanogaster* in 2002 [25], various ZF-effector combinations have been applied in genome bioediting of diverse organisms including flies, moths, zebrafish, rats, and humans [21, 26]. Following the pioneering work done with ZF-effectors, genome bioediting using TALE-effectors advanced rapidly since the first TALENs were reported in 2010 [27]. ZFNs and TALENs are also applied to generate genetically engineered crop plants, such as herbicide-tolerant *Zea mays* [28] and disease-resistant rice [29]. Some bacteria and archaea genomes contain the CAS protein operon followed by CRISPR arrays, which are composed of direct repeats interspersed by small segments (protospacers) adopted from invading DNAs. Transcription of a CRISPR array, followed by enzymatic cleavage, yields short mature CRISPR RNA (crRNA). Through base pairing with a protospacer sequence in the invading DNA, crRNA guides the targeted degradation of invading DNA by recruiting CAS nucleases. A CRISPR/CAS genome bioediting system was developed based on the Type II CRISPR system from *Streptococcus pyogenes*, which contains the minimal CRISPR machinery composed of a single CAS9 protein, a crRNA with complementary sequence to the target site, and a trans-activating RNA (tracrRNA) that forms a hairpin with crRNA. A modified CRISPR/CAS9 system has been shown to drive targeted DNA cleavage in vitro [30, 31] and was also used to induce mutations and edit genetic loci of interest in eukaryotes such as mouse and human cell lines [32, 33], but thus far not in plants. RNA-guided genome editing avoids intrinsic limitations in protein-guided genome editing, such as off-target mutagenesis activity due to imperfect protein-DNA recognition. RNA-guiding sequence in crRNA is readily programmable compared to the substantial effort required to generate customized DNA binding proteins. CRISPR/CAS9 also offers the possibility of multiplex genome bioediting. In addition, the CAS9 protein can be mutated to DNA nickase [30] to promote precise genome editing through HR. Cong et al. [32, 33] consistently detected no indels induced by a CRISPR/CAS nickase system [32, 33]. When a homology repair tem-plate was provided, a pair of restriction sites was inserted precisely into the target loci with the CRISPR/CAS nickase system [30]. Despite the apparent benefit of RNA-guided genome bioediting and its broad application potential, the CRISPR/CAS9 bioediting system is still in its infancy. To date, no application of CRISPR/CAS9 has been reported in plants. Extensive studies are required to evaluate its targeting specificity and effectiveness.

Figure 2A:
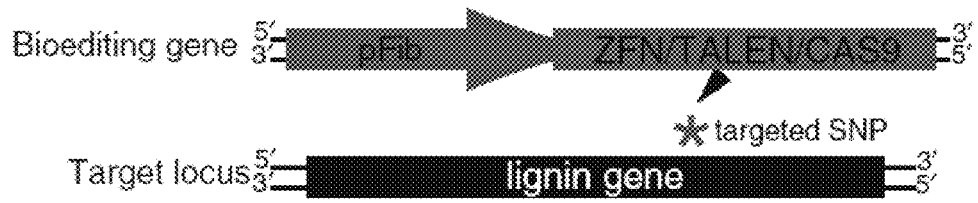
FIG. 2A. New strategies enable multifaceted genetic engineering of plants. Genome bioediting tools. Black box, endogenous lignin locus (target of editing); grey arrow, fiber specific promoter used to drive the expression of the bioediting gene; red box, bioediting gene: ZFNs, TALENs or CRISPR/CAS9; red star, SNP generated when the genome bioediting gene is expressed.
Figure 2B:
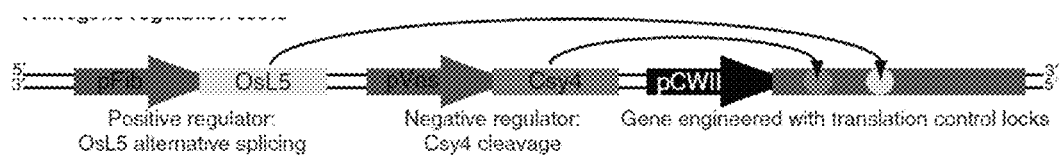
FIG. 2B. New strategies enable multifaceted genetic engineering of plants. Transgene regulation tools. Grey arrow, fiber (pFib) or vessel (pVes) specific promoter; yellow box, gene encoding the OsL5 protein with the alternative splicing cassette shown in the same color inserted in transgenes (yellow circle); blue box, gene encoding the Cys4 protein with its cognition sequence shown in the same color inserted in transgenes (blue circle); black arrow, secondary cell wall promoter (pCWII); red box, engineered gene: gene used to manipulate lignin composition which has been engineered with transgene regulation tool (yellow circle, OsL5 alternative splicing cassette; blue circle, Cys4 cognition sequence).

These genetically encoded bioediting tools could be used to introduce SNPs into essential lignin genes exclusively in targeted tissue such as fiber (FIG. 2). Using a fiber-specific promoter (e.g. pNST, pLAC17) to drive the expression of ZFNs, TALENs or CAS9 designed to recognize the genomic sequence of a key lignin biosynthetic gene (e.g. C4H, C3H, HCT, or CCR1) would repress lignin biosynthesis only in fiber cells without affecting the lignification of vessel cells and other phenylpropanoid-derived pathways active in non-lignified tissues. Such approach would offer greater potentials than the approach developed by Yang et al. [34] that consists of complementing a lignin mutant with a vessel specific promoter which restored the phenylpropanoid pathway only in vessels. However, it is also important to note that expression of biological editing systems has to be tightly controlled, as editing is irreversible and a leaky expression could be lethal to the engineered organism. Therefore, it will be important to use these tools with additional regulatory controls such as those described below.

Transgene Regulation at the Post-Transcriptional Level

The ability to control stringently the spatial and temporal expression of a transgene, as well as its expression level, is an important requirement for successful genetic engineering. It allows optimal tradeoffs such plant fitness versus trait performance (e.g. cell-wall recalcitrance). To attain such perfection, utilization of tissue-specific promoters is rarely sufficient, and additional transcriptional or translation controls typically need to be implemented. The rapid emergence of new technologies will likely offer new opportunities to further optimize transgene expression that will be worthy of further exploration.

In diverse plant lineages, the expression of transcription factor IIIA (TFIIIA) is controlled by a splicing cassette, which includes a regulatory exon flanked by two introns [35]. The regulatory exon encodes a premature termination codon that targets the transcript for nonsense-mediated decay. Binding of ribosomal protein L5 to the splicing cassette triggers exon skipping and allows the expression of the full-length TFIIIA protein. The alternative splicing machinery controlling TFIIIA expression has been adopted to regulate transgene expression [36]. The splicing cassette is structurally modified to interact specifically with rice L5 protein (OsL5) but not endogenous L5 proteins in dicots (such as tobacco or *Arabidopsis*). The insertion of the modified splicing cassette in the encoding sequence of GFP reporter protein showed traceless expression when expressed alone and a ~97-fold expression activation in the presence of OsL5 protein. This result indicates that the expression of a transgene with the splicing cassette inserted in the exon is strictly controlled by the presence of OsL5. This system could be readily adopted as a promoter stacking strategy, that is, when the transgene and OsL5 are expressed under promoters with different characteristics. The resulting expression of the transgene is defined by the activities of both promoters. In CRISPR/CAS machinery, maturation of crRNA requires cleavage in each repeat sequence of the pre-cursor crRNA by dedicated endoRNase [37]. In *Pseudomonas aeruginosa* strain UCBPP-PA14, endoRNase Cys4 selectively recognizes and cleaves a 28-nucleotide (nt) repetitive sequence in the CRISPR repeats [38, 39]. Qi et al. [40] utilized the Cys4 cleavage system in *Escherichia coli* to achieve physical separation of genetic elements of transgenes at the transcript level. In addition, when Cys4 cognition sequence is inserted in frame with a reporter gene, Cys4-controlled transgene silencing was demonstrated in both bacteria and yeast systems [40].

The various lignin manipulation strategies discussed later may be broadly classified into two categories: novel lignin generation and lignin reduction. Generation of novel lignin or monolignol replacement may be introduced into both vessel and fiber tissues by using promoters of lignin biosynthetic genes or secondary cell wall genes to drive transgene expression. However, a promoter-stacking strategy with the OsL5 system may be applied to add strength control for transgene expression. By contrast, lignin reduction strategies using either genome bioediting or transgene expression require a more stringent control, that is, one that is restricted to fiber cells so that vessel lignification occurs normally and the general phenylpropanoid will not be affected constitutively. Such cell-type specificity can be achieved by utilization of the OsL5 or Cys4 systems. With the OsL5 system, the splicing cassette will be introduced into the transgene (e.g. encoding an enzyme that depletes monolignol biosynthesis intermediates) whose expression is driven by lignin (pC4H, pHCT) or other secondary cell wall (pIRX8, pIRX5) promoters of different strengths. OsL5 can be expressed under the control of a fiber-specific promoter (pNST) to further restrict the transgene expression in fiber cells. With the Cys4 system, expression of the transgene (harboring the Cys4 cognition sequence) driven by lignin or other secondary cell wall promoters can be eliminated from vessel cells by expressing Cys4 in vessel cells. Furthermore, it is envisioned that the OsL5 and Cys4 systems can be used to regulate complex multigenic pathways by incorporating the regulatory sequence (the splicing cassette or the Cys4 cognition sequence) into each of the genes to be regulated. In such cases, a single switch for multiple gene regulation would be necessary. A simplified model summarizing the emerging techniques for plant engineering is presented in FIGS. 2A and 2B.

Rerouting the Lignin Pathway and Lignin Replacement by Novel Monolignols Rerouting of the Lignin Pathway The various strategies described previously can be employed to reduce lignin in specific tissues (i.e. fibers) by expressing enzymes that use intermediates from the lignin pathway. For example, the recently described monolignol 4-O-methyltransferase is a promising case study of enzyme engineering conducted specifically to reduce the availability of polymerizable monolignols [13]. More generally, fungi and bacteria are great sources for the discovery of new enzymes active on lignin intermediates, such as the newly characterized caffeoyl-CoA dioxygenase [41]. In a similar fashion, known biosynthetic enzymes could be used to produce several phenylpropanoid-derived metabolites at the expense of lignin. These metabolites includes flavonoids, stilbenes, coumarins, curcuminoids, benzalacetones, hydoxycinnamate esters, and amides synthesized from hydroxycinnamoyl-CoAs; lignans, neolignans, and phenylpropene volatiles such as eugenol and isoeugenol produced from coniferyl alcohol; and benzenoid/phenylpropanoid volatiles derived from phenylalanine and cinnamate. Interestingly, increasing these metabolites may offer other potential benefits in addition to lignin reduction, such as improving resistance to various biotic and abiotic stresses or enhancing a plant's nutritional value. Identification of transport mechanisms for apoplast targeting of some of these phenylpropanoid-derived metabolites should be investigated further. Several biomimetic studies showed their possible coupling with lignin, which, in some cases, resulted in improved cell-wall digestibility or fermentation [42-46]. These observations can be explained by the structure of these metabolites, which have the characteristics of 'novel monolignol candidates' for reducing lignin recalcitrance.

Novel Monolignol Candidates

Figure 1B:
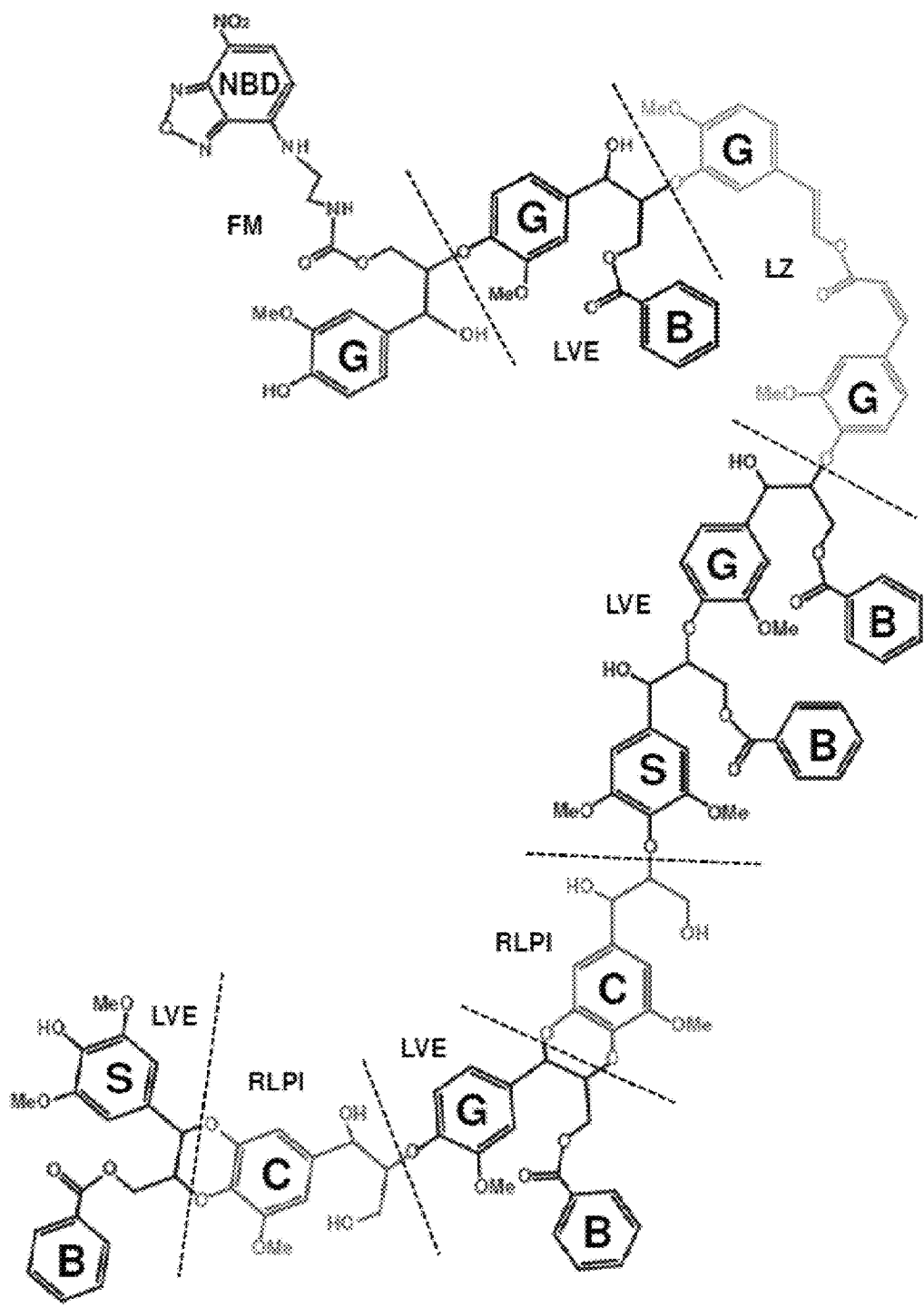
FIG. 1B. Lignin polymer models for lignin bioengineered plants. Bioengineered lignin is exclusively composed of representative unusual monolignols to increase lignin value; to facilitate lignin degradation (lignin zipper); to reduce lignin-polysaccharide interactions; or to fluorescently label lignin. LVE: lignin value enrichment (hydroxycinnamoly benzoate); LZ: lignin zipper (coniferyl ferulate); FM: fluorescent monolignol; RLPI: reduced lignin-polysaccharide interactions (caffeoyl alcohol); C: caffeyl; B: benzoate; S: syringyl; G: guaiacyl; NBD: green nitrobenzofuran.
Figure 3A:
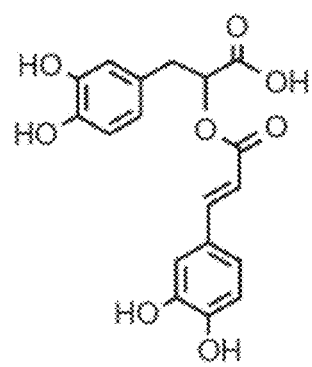
FIG. 3A. An example of a novel monolignol for lignin bioengineering: rosmarinic acid.
Figure 3B:
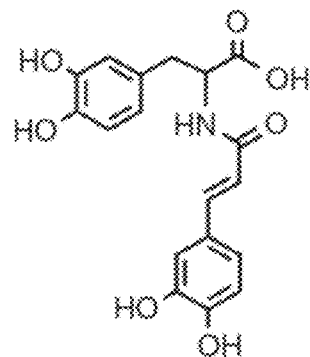
FIG. 3B. An example of a novel monolignol for lignin bioengineering: clovamide.
Figure 3C:
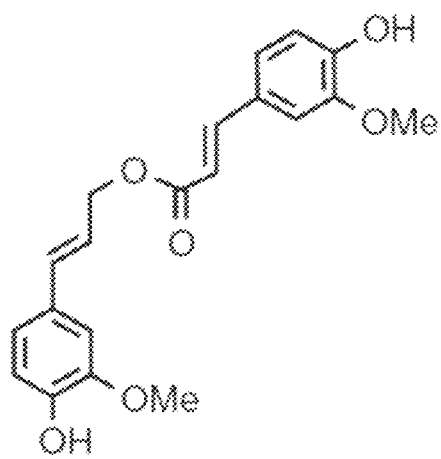
FIG. 3C. An example of a novel monolignol for lignin bioengineering: coniferyl ferulate.

Producing in planta alternative lignin monomers to reduce lignin recalcitrance is a concept that has recently emerged. These monomers should possess a phenolic function containing a hydroxyl group, at the C4 position on the ring, for radicalization and coupling to the lignin. Incorporation of the novel monomers could, depending on their structure, introduce cleavable groups inside the polymer (e.g. coniferyl ferulate and rosmarinic acid); reduce interactions between polysaccharides and lignin (e.g. caffeoyl alcohol); or give rise to lignin with reduced chain lengths (e.g. syringaldehyde) [12, 44, 46, 47] (FIGS. 1B and 4A-4D). Hydroxycinnamates esters and amides: Molecules consisting of hydroxycinnamates conjugated to another phenolic group via an ester or amide bond are potentially cleavable monolignols. These types of dimers would fully incorporate into lignin because of their phenolic groups on both ends, and hence would create some internal alkali- and acid-labile ester and amid bonds within lignin. For example, rosmarinic acid (an ester of caffeate with 3,4-dihydroxyphenyl lactate; FIG. 3A), clovamide (an amide of caffeate with L-dopa; FIG. 3B), and coniferyl ferulate (an ester of ferulate with coniferyl alcohol; FIG. 3C) meet these criteria to introduce labile groups into the lignin backbone. Model studies using biomimetic systems have indeed demonstrated peroxidase-catalyzed polymerization of rosmarinic acid and coniferyl ferulate with conventional monolignols, resulting in enhanced cell wall saccharification after incorporation and mild alkali pretreatment [44,46] (FIGS. 1B and 4A-4D). Monomers that decrease lignin-polysaccharide interactions: The presence of monomers containing catechol or pyrogallol groups would reduce the formation of benzyl ether and ester cross-linking between hemicelluloses and lignin during the b-O-4 coupling of monomers, due to internal trapping of the quinone methide intermediate and the formation of benzodioxane structures [48,49] (FIG. 1B).

Figure 3D:
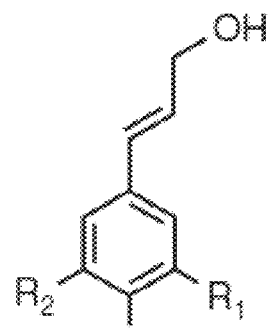
FIG. 3D. An example of a novel monolignol for lignin bioengineering: caffeoyl alcohol ($R_1$=OH, $R_2$=H), 5-hydroxyconiferyl alcohol ($R_1$=OCH$_3$, $R_2$=OH) and 3,4,5-trihydroxycinnamyl alcohol ($R_1$=$R_2$=OH).
Figure 3E:
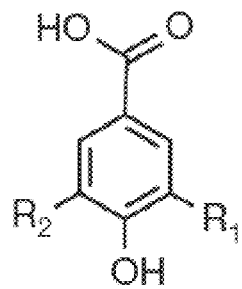
FIG. 3E. An example of a novel monolignol for lignin bioengineering: protochatechuate ($R_1$=OH, $R_2$=H), 5-hydroxyvanillate ($R_1$=OCH$_3$, $R_2$=OH) and gallate ($R_1$=$R_2$=OH).
Figure 3F:
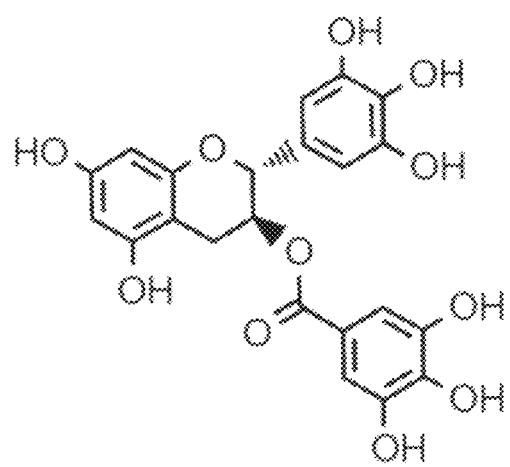
FIG. 3F. An example of a novel monolignol for lignin bioengineering: epigallocatechin gallate.
Figure 3G:
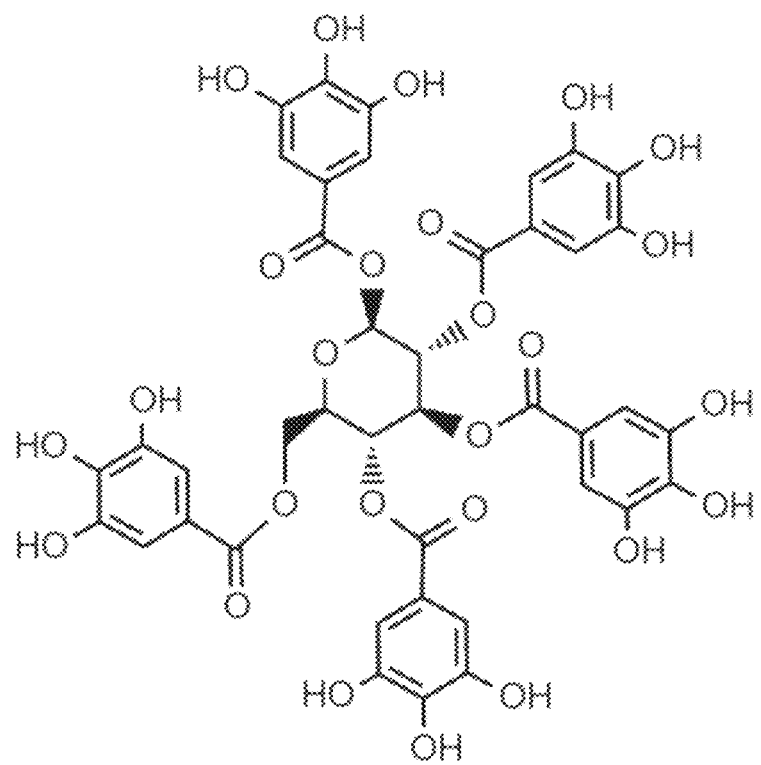
FIG. 3G. An example of a novel monolignol for lignin bioengineering: pentagalloylglucose.
Figure 4A:
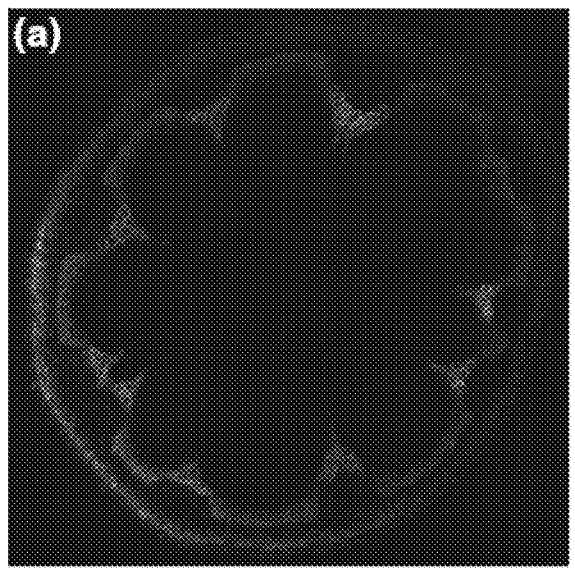
FIG. 4A. Incorporation of NBD-tagged monolignol probe 3G into wild type *Arabidopsis* stems as describe in Tobimatsu et al. 2013 [55]. Transverse sections of a wild type *Arabidopsis* stem fed with NBD-tagged monolignol probe showing exclusive polymerization of the probe in lignifying tissues (interfascicular fibers and xylem cells). Fluorescence in cortical cells comes from cytosolic accumulation of the fluorescent probe. Magnification: 5×.
Figure 4B:
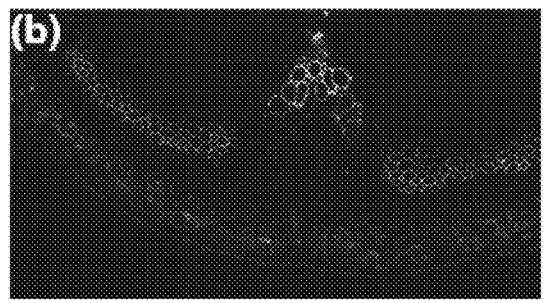
FIG. 4B. Incorporation of NBD-tagged monolignol probe 3G into wild type *Arabidopsis* stems as describe in Tobimatsu et al. 2013 [55]. Transverse sections of a wild type *Arabidopsis* stem fed with NBD-tagged monolignol probe showing exclusive polymerization of the probe in lignifying tissues (interfascicular fibers and xylem cells). Fluorescence in cortical cells comes from cytosolic accumulation of the fluorescent probe. Magnification: 10×.
Figure 4C:
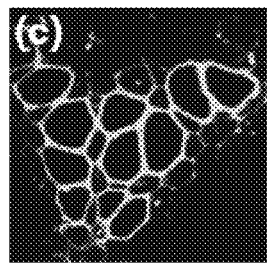
FIG. 4C. Incorporation of NBD-tagged monolignol probe 3G into wild type *Arabidopsis* stems as describe in Tobimatsu et al. 2013 [55]. Transverse sections of a wild type *Arabidopsis* stem fed with NBD-tagged monolignol probe showing exclusive polymerization of the probe in lignifying tissues (interfascicular fibers and xylem cells). Fluorescence in cortical cells comes from cytosolic accumulation of the fluorescent probe. Magnification: 20×.
Figure 4D:
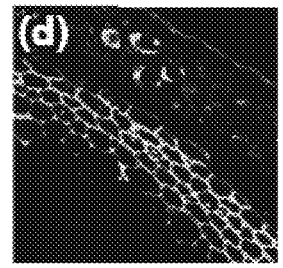
FIG. 4D. Incorporation of NBD-tagged monolignol probe 3G into wild type *Arabidopsis* stems as describe in Tobimatsu et al. 2013 [55]. Transverse sections of a wild type *Arabidopsis* stem fed with NBD-tagged monolignol probe showing exclusive polymerization of the probe in lignifying tissues (interfascicular fibers and xylem cells). Fluorescence in cortical cells comes from cytosolic accumulation of the fluorescent probe. Magnification: 40×.

For example, the b-O-4 polymerization of conventional monolignols with benzene diols such as caffeoyl alcohol and 5-hydroxyconiferyl alcohol (FIG. 3D); or with triols such as 3,4,5-trihydroxycinnamyl alcohol and derivatives of gallate (FIGS. 3D and 3E respectively) should minimize lignin-polysaccharide crosslinkages and enhance cell wall digestibility. Lignins made of caffeoyl alcohol units have been described in seed coats of *Vanilla planifolia* and of several members of the Cactaceae family [50, 51], whereas 5-hydroxyconiferyl alcohol is found in lignins of COMT-deficient plants that were shown to exhibit increased cell wall digestibility [52, 53]. Interestingly, biomimetic studies revealed that incorporation of gallate derivatives such as epigallocatechin gallate and pentagalloylglucose (FIGS. 3F and 3G) into lignin enhances the enzymatic digestion or fermentation of cell walls [42, 43, 45]. Lastly, rosmarinic acid and clovamide, described previously, also fall into the novel monomers category due to their potential to form benzodioxane structures during b-O-4 coupling with conventional monolignols. Monomers that reduce lignin polymerization degree: Overproduction of monomers that initiate or terminate the synthesis of lignin chains should result in a polymer with higher number of shorter molecules. For example, hydroxybenzoates and hydroxybenzaldehydes (C6C1 monomers) couple to conventional monolignols only via their phenolic ring to form lignin 'end-groups.' Our recent worked showed that expressing the bacterial hydroxycinnamoyl-CoA hydratase-lyase (HCHL) in *Arabidopsis* allowed the overproduction of such C6C1 aromatics, which incorporate into the lignin and reduce its molecular weight [12]. Notably, cell walls from these transgenics have improved saccharification but with no reduction of lignin content or biomass yield compared to wildtype plants. C6C1 aromatics containing catechol and pyrogallol groups such as protocatechuate, 5-hydroxyvanillate and gallate, or their aldehyde forms (FIG. 3E) were not detected in the lignin of HCHL plants. Nevertheless, they represent important targets for lignin replacement that would combine the properties of decreasing lignin-polysaccharide interactions and reducing lignin polymerization degree. Monomers that increase lignin value: Based on the capacity of monolignols to attach various compounds, such as fluorphores, onto their C9 position without disturbing their ability to polymerize with lignin monomers and polymers [54, 55] (FIGS. 1B and 4A-4D), a similar approach could be developed to enrich in vivo lignin polymers with free, readily cleavable, and valuable moieties (e.g. benzoate, cinnamate, and tyramine). These lignin 'decorative' moieties would be recovered from lignin after pretreatment during biomass processing and directly used for industrial purposes or as precursors to production of more valuable chemicals. These decorative moieties would be selected based on downstream application, their resistance to polymerization by peroxidase or laccase with other monolignols in vivo, and the existence of acyltransferases capable of coupling them to hydroxycinnamoyl-CoAs. The hydroxycinnamoyl moiety would serve as a carrier since it would polymerize as a conventional monolignol and incorporate the valuable chemical moieties into the lignin polymers. Such processes are already occurring naturally in some species, but at very low levels [1, 56] (FIG. 1B). Alternatively, such monolignol engineering could also be used to change the chemical and physical properties of lignins and facilitate downstream utilization.

Lignin-Engineering Pathways

Several type III polyketide synthases have been characterized for the synthesis of flavonoids, stilbenes, coumarins, curcuminoids, and benzalacetones in various plant species [57], but the impact of overexpressing them in tissues developing lignified secondary cell walls has never been investigated. Providing that there is a sufficient amount of the co-substrate malonyl-CoA, these enzymes could be used to reroute hydroxycinnamoyl-CoAs away from the lignin pathway. Similarly, enzymes involved in the synthesis of lignans and neolignans could be used to reroute coniferyl alcohol away from lignin formation [58], and the precursors phenylalanine, cinnamate, and coniferyl alcohol could be converted by different enzymes into benzenoid/phenylpropanoid volatiles at the expense of lignin synthesis [59].

The tissue-specific overexpression of several enzymes from the BAHD acyl-CoA transferase family [60] is of particular interest for the production of cleavable monolignol candidates. For example, several transferases that catalyze the synthesis of hydroxycinnamate esters such as rosmarinic acid and coniferyl ferulate/coumarate have been identified within this family [61-63]. However, besides hydroxycinnamoyl/benzoyl-CoA:anthranilate N-hydroxycinnamoyl/benzoyltransferase (HCBT) from carnation, and hydroxycinnamoyl-CoA:hydroxyanthranilate N-hydroxycinnamoyltransferase (HHT) from oats—which couple hydroxcinnamoyl-CoAs to (hydroxyl)anthranilates [12, 64]—no BAHDs catalyzing the synthesis of hydroxycinnamate amides using aromatic acceptors have been identified. However, several N-phenylpropenoyl-aromatic amino acid amides, such as (deoxy)clovamide, are found in various plant species [65]. Instead, enzymes responsible for the synthesis of hydroxycinnamate amides of tyramine, other potential cleavable monolignols, were found to belong to the GCN5-related N-acyltransferase family (GNAT) [66,67].

More generally, overexpression of monolignol acyltransferases that use (hydroxy)benzoyl-CoA as a donor, which still remain to be discovered, could potentially be used to produce monomers to reduce lignin DP and enrich it with valuable moieties that could be recovered during biomass processing [68].

Biosynthetic enzymes for the production of C6C1 compounds have been described in plants. In particular, three enzymes from the vanilla orchid have been implied in the synthesis of vanillin from coumarate via the intermediates 4-hydroxybenzaldehyde and protocatechualdehyde [69-71]. Therefore, co-expressing theses enzymes in lignifying tissues could reroute coumarate towards the synthesis of these C6C1 aromatics. Alternatively, HCHL enzymes can be used for the conversion of hydroxycinnamoyl-CoAs into C6C1 hydroxybenzaldehydes. Expression of HCHL in *Arabidopsis* showed that C6C1 hydroxybenzaldehydes were efficiently converted by endogenous enzymes to the corresponding C6C1 acids and could undergo hydroxylation and methoxylation of their aromatic ring [12]. Finally, bacterial chorismate pyruvate-lyase such as UbiC from *Escherichia coli* can be used for in-planta accumulation of 4-hydroxybenzoate from chorismate [72,73], whereas bacterial 4-hydroxybenzoate-3-hydroxylases can be used for protocatechuate production [74].

Concerning the synthesis of pyrogallol groups, a study reported a fivefold increase of gallate content in tobacco plants that overexpress the shikimate dehydrogenase from walnut (*Juglans regia*) or from *E. coli* [75]. We recently reported that the bacterial coumarate 3-hydroxylase Sam5 from *Saccharothrix espanaensis* was able to hydroxylate caffeate to produce 3,4,5-trihydroxycinnamate when expressed in *E. coli* [12]. This discovery opens an opportunity to reroute coumarate from the lignin pathway and to produce in planta molecules with pyrogallol groups.

CONCLUSION

Although the lignin biosynthesis pathway and its enzymes are well characterized, lignin reduction remains a challenging task. This problem stems from a lack of specificity in traditional lignin-reduction methods, which usually compromise plant growth or impair the plant defense system. Emerging strategies like genome bioediting and transgene regulation provide new options to achieve controlled lignin manipulations in targeted plant tissues when applied in conjunction with tissue-type-specific or cell-type-specific promoters. It will finally give the opportunity to design crops with optimized lignin composition and distribution while retaining all other traits related to the phenylpropanoid pathway. Besides traditional lignin reduction methods that directly target genes from the lignin biosynthetic pathway, novel dominant approaches are currently in development. This new trend for lignin engineering focuses on the redirection of carbon flux to the production of related phenolic com-pounds and on the replacement of monolignols with novel lignin monomers to improve biophysical and chemical properties of lignins such as recalcitrance, or industrial use. These novel technologies require experimental validation, as several have yet to be tested in plants or crops, but they are worthy of attention because they offer both economic potential and an intellectual challenge to the research community.

REFERENCES CITED

1. Boerjan W, Ralph J, Baucher M: Lignin biosynthesis. Annu Rev Plant Biol 2003, 54:519-546.
2. Blanch H W, Simmons B A, Klein-Marcuschamer D: Biomass deconstruction to sugars. Biotechnol J 2011, 6:1086-1102.
3. Hamelinck C N, Hooijdonk Gv, Faaij A P C: Ethanol from lignocellulosic biomass: techno-economic performance in short-, middle- and long-term. Biomass Bioenergy 2005, 28:384-410.
4. Baucher M, Halpin C, Petit-Conil M, Boerjan W: Lignin: genetic engineering and impact on pulping. Crit Rev Biochem Mol Biol 2003, 38:305-350.
5. Jung H G, Allen M S: Characteristics of plant cell walls affecting intake and digestibility of forages by ruminants. J Anim Sci 1995, 73:2774-2790.
6. Umezawa T: The cinnamate/monolignol pathway. Phytochem Rev 2010, 9:1-17.
7. Weng J K, Chapple C: The origin and evolution of lignin biosynthesis. New Phytol 2010, 187:273-285.
8. Bonawitz N D, Chapple C: Can genetic engineering of lignin deposition be accomplished without an unacceptable yield penalty? Curr Opin Biotechnol 2013, 24:336-343.
9. Li X, Weng J K, Chapple C: Improvement of biomass through lignin modification. Plant J 2008, 54:569-581.
10. Brosnan C A, Voinnet O: Cell-to-cell and long-distance siRNA movement in plants: mechanisms and biological implications. Curr Opin Plant Biol 2011, 14:580-587.
11. Vogt T: Phenylpropanoid biosynthesis. Mol Plant 2010, 3:2-20.
12. Eudes A, George A, Mukerjee P, Kim J S, Pollet B, Benke P I, Yang F, Mitra P, Sun L, Cetinkol O P et al.: Biosynthesis and incorporation of side-chain-truncated lignin monomers to reduce lignin polymerization and enhance saccharification. Plant Biotechnol J 2012, 10:609-620. This article reports on the in-planta expression of a bacterial phenylpropanoid side-chain cleavage enzyme for the production of C6C1 lignin monomers. Lignin from the engineered plants incorporates higher amount of C6C1 monomers and has a lower degree of polymerization, which result in higher biomass saccharification yields. Efforts were made to engineer only lignifying tissues by using a secondary cell wall-specific promoter.
13. Zhang K, Bhuiya M-W, Pazo J R, Miao Y, Kim H, Ralph J, Liu C-J: An engineered monolignol 4-O-methyltransferase depresses lignin biosynthesis and confers novel metabolic capability in *arabidopsis*. Plant Cell Online 2012, 24:3135-3152. This article reports the engineering and in-planta expression of a monolignol 4-O-methyltransferase. *Arabidopsis* plants expressing the created enzyme produce non polymerizable para-methoxylated monolignols, have reduced lignin contents, and show higher biomass saccharification yields. This study is a rare example of protein engineering applied to plant metabolic engineering
14. Vanholme R, Storme V, Vanholme B, Sundin L, Christensen J H, Goeminne G, Halpin C, Rohde A, Morreel K, Boerjan W: A systems biology view of responses to lignin biosynthesis perturbations in *Arabidopsis*. Plant Cell 2012, 24:3506-3529. This article presents a great overview of multiple changes in response to perturbation of the phenylpropanoid pathway. It uses a system biology approach to better understand lignin biosynthesis and aromatic metabolic network.
15. Zhong R, Lee C, Ye Z-H: Evolutionary conservation of the transcriptional network regulating secondary cell wall biosynthesis. Trends Plant Sci 2010, 15:625-632.

16. Berthet S, Demont-Caulet N, Pollet B, Bidzinski P, Cezard L, Le Bris P, Borrega N, Herve J, Blondet E, Balzergue S et al.: Disruption of LACCASE4 and 17 results in tissue-specific alterations to lignification of *Arabidopsis thaliana* stems. Plant Cell 2011, 23:1124-1137.
17. Bollhöner B, Prestele J, Tuominen H: Xylem cell death: emerging understanding of regulation and function. J Exp Botany 2012, 63:1081-1094.
18. Ko J-H, Kim H-T, Hwang I, Han K-H: Tissue-type-specific transcriptome analysis identifies developing xylem-specific promoters in poplar. Plant Biotechnol J 2012, 10:587-596.
19. Kubo M, Udagawa M, Nishikubo N, Horiguchi G, Yamaguchi M, Ito J, Mimura T, Fukuda H, Demura T: Transcription switches for protoxylem and metaxylem vessel formation. Genes Develop 2005, 19:1855-1860.
20. Mitsuda N, Iwase A, Yamamoto H, Yoshida M, Seki M, Shinozaki K, Ohme-Takagi M: NAC transcription factors, NST1 and NST3, are key regulators of the formation of secondary walls in woody tissues of *Arabidopsis*. Plant Cell Online 2007, 19:270-280.
21. Gaj T, Gersbach C A, Barbas C F 3rd: ZFN, TALEN, and CRISPR/Cas-based methods for genome engineering. Trends Biotechnol 2013, 31:397-405. This review summarized the development and recent advances in ZFN, TALEN, and CRISPR/CAS systems. Advances and potential drawbacks of each method are also discussed and presented to readers.
22. Boch J, Scholze H, Schornack S, Landgraf A, Hahn S, Kay S, Lahaye T, Nickstadt A, Bonas U: Breaking the code of DNA binding specificity of TAL-type III effectors. Science 2009, 326:1509-1512.
23. Moore M, Klug A, Choo Y: Improved DNA binding specificity from polyzinc finger peptides by using strings of two-finger units. Proc Natl Acad Sci 2001, 98:1437-1441.
24. Moscou M J, Bogdanove A J: A simple cipher governs DNA recognition by TAL effectors. Science 2009, 326:1501.
25. Bibikova M, Golic M, Golic K G, Carroll D: Targeted chromosomal cleavage and mutagenesis in *Drosophila* using zinc-finger nucleases. Genetics 2002, 161:1169-1175.
26. Carroll D: Zinc-finger nucleases: a panoramic view. Curr Gene Therapy 2011, 11:2-10.
27. Christian M, Cermak T, Doyle E L, Schmidt C, Zhang F, Hummel A, Bogdanove A J, Voytas D F: Targeting DNA double-strand breaks with TAL effector nucleases. Genetics 2010, 186:757-761.
28. Shukla V K, Doyon Y, Miller J C, DeKelver R C, Moehle E A, Worden S E, Mitchell J C, Arnold N L, Gopalan S, Meng X et al.: Precise genome modification in the crop species *Zea mays* using zinc-finger nucleases. Nature 2009, 459:437-441.
29. Li T, Liu B, Spalding M H, Weeks D P, Yang B: High-efficiency TALEN-based gene editing produces disease-resistant rice. Nat Biotechnol 2012, 30:390-392. This article reports a great application of TALENs in plant engineering.
30. Gasiunas G, Barrangou R, Horvath P, Siksnys V: Cas9-crRNA ribonucleoprotein complex mediates specific DNA cleavage for adaptive immunity in bacteria. Proc Natl Acad Sci 2012, 109:E2579-E2586.
31. Jinek M, Chylinski K, Fonfara I, Hauer M, Doudna J A, Charpentier E: A programmable dual-RNA-guided DNA endonuclease in adaptive bacterial immunity. Science 2012, 337:816-821. This article reports that CAS9 proteins of Type II CRISPR/CAS system from *Streptococcus pyogenes* require a base-paired structure formed between the crRNA and the tracrRNA to cleave target dsDNA. Such system is modified to achieve sequence-specific dsDNA cleavage using CAS9 protein and a chimeric RNA molecule mimicking the structure formed by crRNA and tracrRNA. The authors proposed for the first time the utilization of RNA guided CAS9 in genome editing.
32. Cong L, Ran F A, Cox D, Lin S, Barretto R, Habib N, Hsu P D, Wu X, Jiang W, Marraffini L A et al.: Multiplex genome engineering using CRISPR/Cas systems. Science 2013, 339:819-823.
33. Mali P, Yang L, Esvelt K M, Aach J, Guell M, DiCarlo J E, Norville J E, Church G M: RNA-guided human genome engineering via Cas9. Science 2013, 339:823-826. This article is the first report using the CRISPR/CAS system to perform single and multiple edits in eukaryote genome.
34. Yang F, Mitra P, Zhang L, Prak L, Verhertbruggen Y, Kim J S, Sun L, Zheng K, Tang K, Auer M et al.: Engineering secondary cell wall deposition in plants. Plant Biotechnol J 2013, 11:325-335.
35. Hammond M C, Wachter A, Breaker R R: A plant 5S ribosomal RNA mimic regulates alternative splicing of transcription factor IIIA pre-mRNAs. Nat Struct Mol Biol 2009, 16:541-549.
36. Hickey S F, Sridhar M, Westermann A J, Qin Q, Vijayendra P, Liou G, Hammond M C: Transgene regulation in plants by alternative splicing of a suicide exon. Nucl Acids Res 2012, 40:4701-4710. This article demonstrates for the first time the effectiveness of the OsL5 associated alternative splicing system in conferring robust transgene activation with no background expression in planta. More importantly, minimal gene context requirement for the cassette insertion has been identified, implicating broad application potential of the system.
37. Wiedenheft B, Sternberg S H, Doudna J A: RNA-guided genetic silencing systems in bacteria and archaea. Nature 2012, 482:331-338.
38. Haurwitz R E, Jinek M, Wiedenheft B, Zhou K, Doudna J A: Sequence- and structure-specific RNA processing by a CRISPR endonuclease. Science 2010, 329:1355-1358.
39. Przybilski R, Richter C, Gristwood T, Clulow J S, Vercoe R B, Fineran P C: Csy4 is responsible for CRISPR RNA processing in *Pectobacterium atrosepticum*. Rna Biol 2011, 8:517-528.
40. Qi L, Haurwitz R E, Shao W, Doudna J A, Arkin A P: RNA processing enables predictable programming of gene expression. Nat Biotech 2012, 30:1002-1006. This article is the first report related the application of CRISPR-based RNA as synthetic biology tool to regulate the expression of synthetic genes in *E. coli*, *B. subtilis* and *S. cerevisiae*. It also demonstrates that the different genetic elements can be dissociated and used to regulated gene expression in foreign species.
41. Bianchetti C M, Harmann C H, Takasuka T E, Hura G L, Dyer K, Fox B G: Fusion of dioxygenase and lignin-binding domains in a novel secreted enzyme from cellulolytic *Streptomyces* sp. SirexAA-E. J Biol Chem 2013, 288:18574-18587.
42. Elumalai S, Tobimatsu Y, Grabber J H, Pan X, Ralph J: Epigallocatechin gallate incorporation into lignin enhances the alkaline delignification and enzymatic saccharification of cell walls. Biotechnol Biofuels 2012, 5:59.

43. Grabber J, Schatz P, Kim H, Lu F, Ralph J: Identifying new lignin bioengineering targets: 1. Monolignol-substitute impacts on lignin formation and cell wall fermentability. BMC Plant Biol 2010, 10:114.
44. Grabber J H, Hatfield R D, Lu F, Ralph J: Coniferyl ferulate incorporation into lignin enhances the alkaline delignification and enzymatic degradation of cell walls. Biomacromolecules 2008, 9:2510-2516.
45. Grabber J H, Ress D, Ralph J: Identifying new lignin bioengineering targets: impact of epicatechin, quercetin glycoside, and gallate derivatives on the lignification and fermentation of maize cell walls. J Agric Food Chem 2012, 60:5152-5160.
46. Tobimatsu Y, Elumalai S, Grabber J H, Davidson C L, Pan X, Ralph J: Hydroxycinnamate conjugates as potential monolignol replacements: in vitro lignification and cell wall studies with rosmarinic acid. ChemSusChem 2012, 5:676-686.
47. Vanholme R, Morreel K, Darrah C, Oyarce P, Grabber J H, Ralph J, Boerjan W: Metabolic engineering of novel lignin in biomass crops. New Phytol 2012, 196:978-1000. This interesting review provides a comprehensive list of potential alter-native lignin monomers for the reduction of plant biomass recalcitrance.
48. Grabber J H, Hatfield R D: Methyl esterification divergently affects the degradability of pectic uronosyls in nonlignified and lignified maize cell walls. J Agric Food Chem 2005, 53:1546-1549.
49. Grabber J H, Hatfield R D, Ralph J: Apoplastic pH and monolignol addition rate effects on lignin formation and cell wall degradability in maize. J Agric Food Chem 2003, 51:4984-4989.
50. Chen F, Tobimatsu Y, Havkin-Frenkel D, Dixon R A, Ralph J: A polymer of caffeyl alcohol in plant seeds. Proc Natl Acad Sci USA 2012, 109:1772-1777. This is the first literature report of the natural occurrence of catechyl units in lignins.
51. Chen F, Tobimatsu Y, Jackson L, Nakashima J, Ralph J, Dixon R A: Novel seed coat lignins in the Cactaceae: structure, distribution and implications for the evolution of lignin diversity. Plant J 2012, 73:201-211. This is the first literature report of the natural occurrence of 5-hydroxyguaiacyl units in lignins.
52. Fu C, Mielenz J R, Xiao X, Ge Y, Hamilton C Y, Rodriguez M Jr, Chen F, Foston M, Ragauskas A, Bouton J et al.: Genetic manipulation of lignin reduces recalcitrance and improves ethanol production from switchgrass. Proc Natl Acad Sci USA 2011, 108:3803-3808.
53. Van Doorsselaere J, Baucher M, Chognot E, Chabbert B, Tollier M-T, Petit-Conil M, Leplé J-C, Pilate G, Cornu D, Monties B et al.: A novel lignin in poplar trees with a reduced caffeic acid/5-hydroxyferulic acid O-methyltransferase activity. Plant J 1995, 8:855-864.
54. Tobimatsu Y, Davidson C L, Grabber J H, Ralph J: Fluorescence-tagged monolignols: synthesis, and application to studying in vitro lignification. Biomacromolecules 2011, 12:1752-1761.
55. Tobimatsu Y, Wagner A, Donaldson L, Mitra P, Niculaes C, Dima O, Kim J I, Anderson N, Logue D, Boerjan W et al.: Visualization of plant cell wall lignification using fluorescence-tagged monolignols. Plant J 2013, 76:357-366.
56. Sederoff R R, MacKay J J, Ralph J, Hatfield R D: Unexpected variation in lignin. Curr Opin Plant Biol 1999, 2:145-152.
57. Stewart C Jr, Vickery C R, Burkart M D, Noel J P: Confluence of structural and chemical biology: plant polyketide synthases as biocatalysts for a bio-based future. Curr Opin Plant Biol 2013, 16:365-372.
58. Satake H, Ono E, Murata J: Recent advances in the metabolic engineering of lignin biosynthesis pathways for the production of transgenic plant-based foods and supplements. J Agric Food Chem 2013, 61:11721-11729.
59. Colquhoun T A, Clark D G: Unraveling the regulation of floral fragrance biosynthesis. Plant Signal Behav 2011, 6:378-381.
60. D'Auria J C: Acyltransferases in plants: a good time to be BAHD. Curr Opin Plant Biol 2006, 9:331-340.
61. Sander M, Petersen M: Distinct substrate specificities and unusual substrate flexibilities of two hydroxycinnamoyltransferases, rosmarinic acid synthase and hydroxycinnamoyl-CoA:shikimate hydroxycinnamoyltransferase, from *Coleus blumei* Benth. Planta 2011, 233: 1157-1171.
62. Wilkerson C, Ralph J, Withers S: BAHD acyltransferase that synthesizes coniferyl ferulate. U.S. Patent Application Pub. Nos. 20130203973 and 20130219547.
63. Withers S, Lu F, Kim H, Zhu Y, Ralph J, Wilkerson C G: Identification of grass-specific enzyme that acylates monolignols with p-coumarate. J Biol Chem 2012, 287: 8347-8355.
64. Yang Q, Trinh H X, Imai S, Ishihara A, Zhang L, Nakayashiki H, Tosa Y, Mayama S: Analysis of the involvement of hydroxyanthranilate hydroxycinnamoyltransferase and caffeoyl-CoA 3-O-methyltransferase in phytoalexin biosynthesis in oat. Mol Plant Microbe Interact 2004, 17:81-89.
65. Hensel A, Deters A M, Muller G, Stark T, Wittschier N, Hofmann T: Occurrence of N-phenylpropenoyl-L-amino acid amides in different herbal drugs and their influence on human keratinocytes, on human liver cells and on adhesion of *Helicobacter pylori* to the human stomach. Planta Med 2007, 73:142-150.
66. Schmidt A, Grimm R, Schmidt J, Scheel D, Strack D, Rosahl S: Cloning and expression of a potato cDNA encoding hydroxycinnamoyl-CoA:tyramine N-(hydroxycinnamoyl)transferase. J Biol Chem 1999, 274:4273-4280.
67. Vetting M W, SdC L P, Yu M, Hegde S S, Magnet S, Roderick S L, Blanchard J S: Structure and functions of the GNAT superfamily of acetyltransferases. Arch Biochem Biophys 2005, 433:212-226.
68. Ralph J, Akiyama T, Coleman H, Mansfield S: Effects on lignin structure of coumarate 3-hydroxylase downregulation in poplar. Bioenergy Research 2012, 5:1009-1019.
69. Podstolski A, Havkin-Frenkel D, Malinowski J, Blount J W, Kourteva G, Dixon R A: Unusual 4-hydroxybenzaldehyde synthase activity from tissue cultures of the vanilla orchid *Vanilla planifolia*. Phytochemistry 2002, 61:611-620.
70. Pak F E, Gropper S, Dai W D, Havkin-Frenkel D, Belanger F C: Characterization of a multifunctional methyltransferase from the orchid *Vanilla planifolia*. Plant Cell Rep 2004, 22:959-966.
71. Dixon R A, Havkin-Frenkel D, Podstolski A: Vanillin biosynthetic pathway enzyme from vanilla planif. US Patent 2003, WO2003071861 A3.
72. Siebert M, Sommer S, Li S M, Wang Z X, Severin K, Heide L: Genetic engineering of plant secondary metabolism. Accumulation of 4-hydroxybenzoate glucosides as a result of the expression of the bacterial ubiC gene in tobacco. Plant Physiol 1996, 112:811-819.
73. Viitanen P V, Devine A L, Khan M S, Deuel D L, Van Dyk D E, Daniell H: Metabolic engineering of the chloroplast genome using the *Escherichia coli* ubiC gene reveals that chorismate is a readily abundant plant precursor for p-hydroxybenzoic acid biosynthesis. Plant Physiol 2004, 136:4048-4060.
74. Alt S, Burkard N, Kulik A, Grond S, Heide L: An artificial pathway to 3,4-dihydroxybenzoic acid allows generation of new aminocoumarin antibiotic recognized by catechol transporters of *E. coli*. Chem Biol 2011, 18:304-313.
75. Muir R M, Ibanez A M, Uratsu S L, Ingham E S, Leslie C A, McGranahan G H, Batra N, Goyal S, Joseph J, Jemmis E D et al.: Mechanism of gallic acid biosynthesis in bacteria (*Escherichia coli*) and walnut (*Juglans regia*). Plant Mol Biol 2011, 75:555-565.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A cell wall or biomass obtained from a genetically modified plant comprising a nucleic acid encoding a promoter operatively linked to an open reading frame (ORF) encoding an exogenous acyltransferase wherein the acyltransferase catalyzes the addition of an acceptor to a lignin carrier moiety; and a lignin polymer comprising the lignin carrier moiety with the acceptor; wherein the promoter is a fiber-specific promoter, a vessel-specific promoter, or a secondary cell wall promoter; the acyltransferase is hydroxycinnamoyl/benzoyl-CoA:anthranilate N-hydroxycinnamoyl/benzoyltransferase (HCBT), or hydroxycinnamoyl-CoA:hydroxyanthranilate N-hydroxycinnamoyltransferase (HHT); and the acceptor is a (hydroxyl)anthranilate; and the lignin polymers have an average molecular weight that is lower than the average molecular weight of the lignin polymers of the plant that is not genetically modified.

2. A method to produce lignin modified with an acceptor, comprising: (a) providing a genetically modified plant comprising a nucleic acid encoding a promoter operatively linked to an open reading frame (ORF) encoding an exogenous acyltransferase wherein the acyltransferase catalyzes the addition of an acceptor to a lignin carrier moiety; and a lignin polymer comprising the lignin carrier moiety with the acceptor; wherein the promoter is a fiber-specific promoter, a vessel-specific promoter, or a secondary cell wall promoter; the acyltransferase is hydroxycinnamoyl/benzoyl-CoA:anthranilate N-hydroxycinnamoyl/benzoyltransferase (HCBT), or hydroxycinnamoyl-CoA:hydroxyanthranilate N-hydroxycinnamoyltransferase (HHT); and the acceptor is a (hydroxyl)anthranilate; and the lignin polymers have an average molecular weight that is lower than the average molecular weight of the lignin polymers of the plant that is not genetically modified, (b) growing the genetically modified plant, (c) isolating the lignin of the plant from the rest of the plant, and (d) separating the acceptors from the lignin.

3. The cell wall or biomass of claim 1, wherein the promoter is the fiber-specific promoter.

4. The cell wall or biomass of claim 3, wherein the fiber-specific promoter is pNST or pLAC17.

5. The cell wall or biomass of claim 1, wherein the promoter is the vessel-specific promoter.

6. The cell wall or biomass of claim 1, wherein the promoter is the secondary cell wall promoter.

7. The cell wall or biomass of claim 6, wherein the secondary cell wall promoter is pIRX8 or pIRX5.

8. The method of claim 2, wherein the promoter is the fiber-specific promoter.

9. The method of claim 8, wherein the fiber-specific promoter is pNST or pLAC17.

10. The method of claim 2, wherein the promoter is the vessel-specific promoter.

11. The method of claim 2, wherein the promoter is the secondary cell wall promoter.

12. The method of claim 11, wherein the secondary cell wall promoter is pIRX8 or pIRX5.

* * * * *